(12) United States Patent
Oba

(10) Patent No.: US 11,389,037 B2
(45) Date of Patent: Jul. 19, 2022

(54) TOILET ROLL

(71) Applicant: DAIO PAPER CORPORATION, Shikokuchuo (JP)

(72) Inventor: Shintaro Oba, Shizuoka (JP)

(73) Assignee: DAIO PAPER CORPORATION, Ehime (JP)

( * ) Notice: Subject to any disclaimer, the term of this patent is extended or adjusted under 35 U.S.C. 154(b) by 0 days.

(21) Appl. No.: 17/059,450

(22) PCT Filed: Jun. 3, 2019

(86) PCT No.: PCT/JP2019/021963
§ 371 (c)(1),
(2) Date: Nov. 29, 2020

(87) PCT Pub. No.: WO2019/235417
PCT Pub. Date: Dec. 12, 2019

(65) Prior Publication Data
US 2021/0204764 A1    Jul. 8, 2021

(30) Foreign Application Priority Data
Jun. 4, 2018    (JP) .............. JP2018-107230

(51) Int. Cl.
*A47K 10/22*    (2006.01)
*A61L 9/01*    (2006.01)
(52) U.S. Cl.
CPC ............ *A47K 10/22* (2013.01); *A61L 9/01* (2013.01)

(58) Field of Classification Search
None
See application file for complete search history.

(56) References Cited

U.S. PATENT DOCUMENTS

| | | | | |
|---|---|---|---|---|
| 2,639,939 A | * | 5/1953 | Henry | A47K 10/32 242/599.3 |
| 6,425,530 B1 | * | 7/2002 | Coakley | A61L 9/04 239/52 |
| 7,850,038 B2 | * | 12/2010 | Mueller | B65D 77/24 221/45 |
| 2001/0024731 A1 | * | 9/2001 | Usui | B32B 27/10 428/537.5 |
| 2005/0001051 A1 | * | 1/2005 | Dobler | A61L 9/042 239/34 |

(Continued)

FOREIGN PATENT DOCUMENTS

| | | | |
|---|---|---|---|
| CA | 2 622 029 | * | 3/2007 |
| JP | S56-111890 U | | 8/1981 |

(Continued)

*Primary Examiner* — William A. Rivera
(74) *Attorney, Agent, or Firm* — Renner, Kenner; Arthur M. Reginelli

(57) ABSTRACT

To provide a toilet roll having a deodorizing function.
The problem is solved by a toilet roll in which a volatile deodorizing fragrant agent that is vaporized to emit fragrance and chemically deodorizes a malodorous component is applied to an outer periphery of a paper tube, and a deodorizing region to which a deodorant that chemically deodorizes a malodorous component is applied for deodorizing a malodorous component by contact with the malodorous component is provided on an inner periphery of the paper tube.

3 Claims, 1 Drawing Sheet

(56) References Cited

U.S. PATENT DOCUMENTS

| | | | | |
|---|---|---|---|---|
| 2005/0069665 A1* | 3/2005 | Butler, III | ............... | A47K 10/16 |
| | | | | 428/36.9 |
| 2012/0097790 A1* | 4/2012 | Wilkins | ................ | B65H 75/08 |
| | | | | 242/599.2 |
| 2013/0136713 A1* | 5/2013 | Terada | .................... | A61L 9/013 |
| | | | | 424/76.1 |
| 2013/0199557 A1* | 8/2013 | Maertz | .................... | A61F 7/034 |
| | | | | 132/200 |
| 2014/0231568 A1* | 8/2014 | Mellin | ................... | B65H 75/10 |
| | | | | 242/160.1 |
| 2015/0272403 A1* | 10/2015 | Silverman | ............... | A47K 10/16 |
| | | | | 15/104.93 |
| 2015/0320267 A1* | 11/2015 | Pour | ...................... | A47K 10/46 |
| | | | | 242/398 |
| 2017/0232135 A1* | 8/2017 | Woo | ......................... | A61L 15/46 |
| | | | | 604/359 |
| 2018/0179706 A1* | 6/2018 | Moriwaki | ............ | D21H 5/0005 |
| 2019/0110648 A1 | 4/2019 | Moriwaki | | |
| 2020/0040529 A1* | 2/2020 | Rouse | .................... | D21H 11/12 |

FOREIGN PATENT DOCUMENTS

| | | |
|---|---|---|
| JP | 2014-193213 A | 10/2014 |
| JP | 2016-019738 A | 2/2016 |
| JP | 2017-176581 A | 10/2017 |

\* cited by examiner

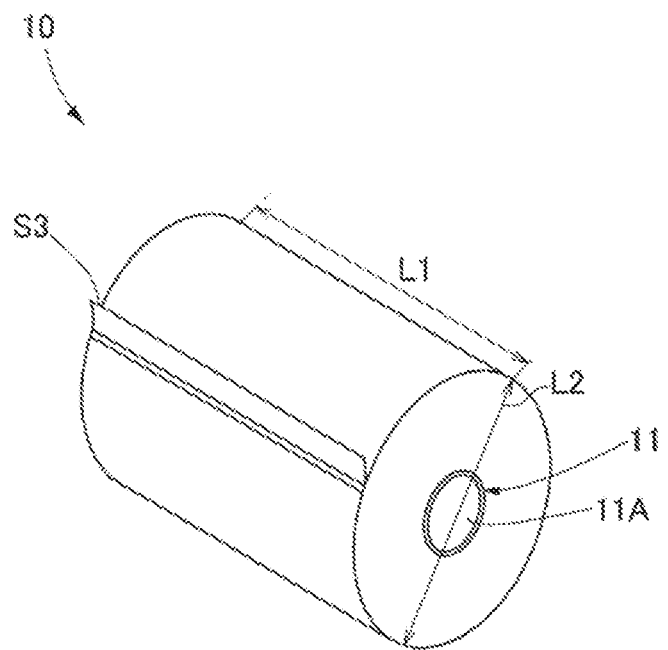

ated in a toilet space, there is a known technique of
TOILET ROLL

TECHNICAL FIELD

The present invention relates to a toilet roll obtained by winding belt shaped toilet paper around a paper tube.

BACKGROUND ART

In order to alleviate or deodorize an ammonia odor generated in a toilet space, there is a known technique of coating an inner surface of a paper tube of a toilet roll that is stocked in the toilet space with a deodorant or the like to cause the inner surface of the paper tube to carry the deodorant or the like (see Patent Literature 1 below).

In addition, there is also a known deodorizing technique performed by modulating or masking malodor by fragrance applied to a paper tube or toilet paper. (Patent Literature 2 below). Furthermore, there is also a known technique of impregnating a paper tube with a deodorant that exhibits a deodorizing effect by a neutralizing effect by utilizing a fact that ammonia, which causes odor, is strongly basic (Patent Literature 3 below).

CITATION LIST

Patent Literature

Patent Literature 1: JP S56-111890 Y
Patent Literature 2: JP 2017-176571 A
Patent Literature 3: JP 2016-19738 A

SUMMARY OF INVENTION

Technical Problem

However, the technique of coating an inner surface of a paper tube of a toilet roll with a deodorant or the like to cause the inner surface of the paper tube to carry the deodorant or the like has a problem in the available percentage of the deodorant because the amount of the deodorant carried on the inner surface is small, and the deodorant is covered to no small extent with an adhesive component serving as a binder.

In addition, the deodorizing technique performed by modulating or masking malodor by fragrance does not decompose the malodor itself, and therefore has a problem that a large amount of fragrant agent is used. Therefore, it is difficult to apply a sufficient amount of fragrant agent necessary for masking or the like to a limited site such as a paper tube, and there is a problem that malodor is not sufficiently masked. Furthermore, there is also a problem that fragrance itself due to the fragrant agent tends to be excessively strong although the fragrance is not sufficient for masking.

Furthermore, the technique of impregnating a paper tube with a deodorant that exhibits a deodorizing effect by a neutralizing effect is excellent in neutralizing and decomposing ammonia itself, but requires contact between ammonia or the like to be deodorized and the deodorant. Therefore, there is a problem that an immediate effect on ammonia diffused in a toilet space cannot be expected. In addition, it is difficult to suppress even a urine odor emitted by urine scattered on a wall or a floor at a distance from the paper tube to which the deodorant is applied. In addition, the technique of applying a deodorant to a paper tube has a problem that it is difficult to recognize whether or not an effect of the deodorant applied to the paper tube is exhibited.

Therefore, a main object of the present invention is to provide a toilet roll from which a deodorant is not detached, which has an excellent immediate effect on a malodorous component such as ammonia diffused in a toilet space, and an excellent deodorizing effect on an odor source and excellent sustainability of the deodorizing effect, and which makes it easy to recognize exhibition of the deodorizing effect.

Solution to Problem

A first means for solving the above problems is
a toilet roll including a paper tube, and belt shaped toilet paper wound around the paper tube, in which
a volatile deodorizing fragrant agent that is vaporized to emit fragrance and chemically deodorizes a malodorous component is applied to an outer periphery of a paper tube, and a deodorizing region to which a deodorant that chemically deodorizes a malodorous component is applied for deodorizing a malodorous component by contact with the malodorous component is provided on an inner periphery of the paper tube.

A second means is
the toilet roll according to the first means, in which the deodorant contains any one of polyphenol, a polyphenol derivative, and a polyphenol analog.

A third means is
the toilet roll according to the first or second means, in which the volatile deodorizing fragrant agent contains one or more kinds of ester-based compounds.

A fourth means is
the toilet roll according to the third means, in which the ester-based compound is selected from the group consisting of linalyl acetate, eugenyl acetate, geranyl acetate, savinyl acetate, sabinene hydrate, citronellyl acetate, terpinyl acetate, neryl acetate, butyl algerate, vetiberyl acetate, benzyl acetate, benzyl benzoate, bornyl acetate, bornyl isovalerate, methyl anthranilate, methyl salicylate, methyl butyrate, methyl benzoate, menthyl acetate, labansuryl acetate, and formate.

A fifth means is
the toilet roll according to the third means, in which the volatile deodorizing fragrant agent contains at least one of citronellyl formate and phenylethyl formate and does not contain vanillin.

Advantageous Effects of Invention

The present invention described above provides a toilet roll from which a deodorant is not detached, which has an excellent immediate effect on a malodorous component such as ammonia diffused in a toilet space, and an excellent deodorizing effect on an odor source and excellent sustainability of the deodorizing effect, and which makes it easy to recognize exhibition of the deodorizing effect.

BRIEF DESCRIPTION OF DRAWINGS

FIG. 1 is a diagram for explaining a toilet roll according to the present invention.

DESCRIPTION OF EMBODIMENTS

An embodiment of the present invention will be described below with reference to the drawing.

As illustrated in FIG. 1, a toilet roll according to the present invention is obtained by winding belt shaped toilet paper S3 around a paper tube 11. The size and the like of the toilet roll are not limited. However, the toilet roll generally has a width L1 of 100 to 115 mm, a diameter L2 of 100 to 130 mm, a winding length (maximum length of toilet paper) of 18 to 90 m, and a paper tube inner diameter of 35 to 50 mm.

In the present invention, the toilet paper S3 is not particularly limited, and can be publicly known toilet paper having a basis weight per ply of 11.0 to 25.0 g/m$^2$, a paper thickness of 100 to 180 μm, and having about 1 to 4 plies. The basis weight in the present invention means a value measured by a basis weight measuring method of JIS P 8124 (1998). The paper thickness means a value obtained by sufficiently subjecting a test piece to humidity control under conditions of JIS P 8111 (1998), then measuring the paper thickness five times using a dial thickness gauge (thickness measuring instrument) "PEACOCK G type" (manufactured by Ozaki MFG. Co., Ltd.) under the same conditions, and calculating an average of the measured values. Note that a pressure applied during the measurement is about 70 gf.

In a toilet roll 10 according to the present invention, characteristically, a volatile deodorizing fragrant agent that chemically deodorizes a malodorous component and emits fragrance is applied to an outer periphery of a paper tube. Since the toilet roll 10 is obtained by winding toilet paper around an outer periphery of a paper tube, the volatile deodorant applied to the outer periphery of the paper tube according to the present invention is covered with a layer of the toilet paper. Therefore, the volatile deodorant is not exposed when the toilet roll is used, and fragrance is released with sustained release. That is, in the toilet roll, as the toilet paper is pulled out, a paper layer formed by the wound toilet paper becomes thinner, and therefore a volatilization suppressing effect of the volatile deodorizing fragrant agent decreases. Meanwhile, the amount of the volatile deodorizing fragrant agent applied to the outer periphery also decreases with time due to volatilization. In the toilet roll according to the present invention, since the volatile deodorizing fragrant agent is applied particularly to the outer periphery of the paper tube, it is easy to balance a decrease in the volatility of the volatile deodorizing fragrant agent and a decrease in the volatilization suppressing effect with each other, and excellent sustainability in fragrance and a deodorizing effect is obtained.

In addition, the volatile deodorizing fragrant agent does not exhibit a deodorizing effect in a granular solid state such as zeolite, and is not attached to the outer periphery by a binder. In addition, the outer surface of the paper tube does not rub against a support portion of a toilet roll holder. Therefore, the volatile deodorizing fragrant agent is not detached from the paper tube.

Furthermore, when the volatile deodorizing fragrant agent is applied to the outer surface of the paper tube, there is an advantage in manufacture. When a toilet roll is manufactured, immediately after glue is attached to an outer peripheral surface of a paper tube, toilet paper is wound into a roll. It takes about several seconds, at most about a dozen seconds from the gluing to the start of winding toilet paper. In the toilet roll according to the present invention, the volatile deodorizing fragrant agent is applied to an outer surface of a paper tube. Therefore, the volatile deodorizing fragrant agent can be applied at the same time as the gluing or without a large time lag therefrom, and furthermore the toilet roll can be manufactured in such a manner that the volatile deodorizing fragrant agent is covered with toilet paper immediately after the application. This means that the volatile deodorizing fragrant agent is less likely to be attached to a manufacturing facility during the manufacture, and exposure time of the applied volatile deodorizing fragrant agent can be shortened. Therefore, manufacturing stability is also excellent.

The content of the volatile deodorizing fragrant agent in the toilet roll 10 according to the present invention is not particularly limited. As long as fragrance is felt in a toilet space, the volatile deodorizing fragrant agent is sufficiently effective. The specific content of the volatile deodorizing fragrant agent can be determined in consideration of the specific kind to be used, a deodorizing effect, fragrance, fragrance tone, and the strength of the fragrance.

The volatile deodorizing fragrant agent is a fragrant agent that is volatile at room temperature and emits fragrance by volatilization, but causes a chemical reaction with a malodorous component in a toilet space, and particularly changes the malodorous component into a substance having no or little malodor by a chemical reaction. Note that the malodorous component causes a problem in a toilet space, and is typically ammonia or trimethylamine, which causes a urine odor, or methyl mercaptan or hydrogen sulfide, which causes a stool odor.

The volatile deodorizing fragrant agent emits fragrance by volatilization, and therefore has an excellent immediate effect on a malodorous component such as ammonia diffused in a toilet space. That is, the volatile deodorizing fragrant agent according to the present invention exhibits a deodorizing effect because fragrance having a deodorizing effect is volatilized in a toilet space, and the fragrance promptly comes into contact with a malodorous component such as ammonia diffused in the toilet space. Furthermore, by diffusion of fragrance in the toilet space, the fragrance also comes into contact with urine scattered on a wall or a floor and can also suppress a urine odor emitted by ammonia or the like derived from urine. That is, the volatile deodorizing fragrant agent also has an excellent deodorizing effect on an odor source. Furthermore, the volatile deodorizing fragrant agent is a fragrant agent, therefore makes it easy to recognize the intensity of the deodorizing effect depending on the strength of the fragrance, and makes it possible to recognize a change such as a decrease in deodorizing effect due to a decrease in fragrance or modulation of fragrance.

The volatile deodorizing fragrant agent preferably contains one or more kinds of ester-based compounds. Many kinds of ester-based compounds have a floral fragrance or a fruity fragrance, and are suitable as a fragrant agent used in a toilet space, and can remove or decrease an ammonia odor by an exchange reaction with ammonia, which is a main malodorous component in the toilet space.

Furthermore, the volatile deodorizing fragrant agent may be a fragrant agent having a ketone group or an aldehyde group having a deodorizing effect by a neutralization reaction on an odor having an amine group, typified by ammonia, and can include a fragrant agent having a ketone group or an aldehyde group together with the above ester-based compound.

Examples of a preferable substance as the ester-based compound include linalyl acetate, eugenyl acetate, geranyl acetate, savinyl acetate, sabinene hydrate, citronellyl acetate, terpinyl acetate, neryl acetate, butyl algerate, vetiberyl acetate, benzyl acetate, benzyl benzoate, bornyl acetate, bornyl isovalerate, methyl anthranilate, methyl salicylate, methyl butyrate, methyl benzoate, menthyl acetate, labansuryl acetate, linalyl acetate, and formate. These substances exhibit a high deodorizing effect on ammonia while having fragrance that is felt to be favorable by a human. The volatile deodorizing fragrant agent preferably contains one or more kinds selected from the group.

On the other hand, it is desirable that the ester-based compound has 5 or more carbon atoms. More preferably, specifically, it is desirable that the ester-based compound has 6 to 12 carbon atoms. When the ester-based compound has less than 5 carbon atoms, volatility is too high, and sustainability of fragrance and sustainability of a deodorizing effect are not necessarily sufficient. Particularly, many fragrant agents related to a ester-based compound having 6 to 12 carbon atoms have a vapor pressure in a range of 0.02 mmHg or more and less than 0.1 mmHg at 20° C. in terms of volatility. A fragrant agent having a vapor pressure in this range is called a middle note, has an excellent balance between sustainability and volatility, and can sufficiently exhibit fragrance and a deodorizing effect during a period of use of a toilet roll particularly considering a period during which one toilet roll is generally used up. A ester-based compound having more than 12 carbon atoms may be used. However, a fragrant agent related to a ester-based compound having more than 12 carbon atoms is called a last note, and has slightly inferior prompt volatility.

A particularly preferable volatile deodorizing fragrant agent contains at least one of citronellyl formate and phenylethyl formate. Citronellyl formate and phenylethyl formate can easily have fragrance adjusted to a floral fragrance such as a rose fragrance, emit a fragrance desirable in a toilet space, and have a very good chemical deodorizing effect on a nitrogen source, particularly on ammonia. Furthermore, citronellyl formate and phenylethyl formate have good affinity with a urine odor also in terms of masking properties. In addition, citronellyl formate and phenylethyl formate emit a fragrance tone of middle note with 6 to 12 carbon atoms, and therefore are excellent in terms of a use period and a deodorizing period. In addition, citronellyl formate and phenylethyl formate make it easy to feel fragrance, and make it easy to recognize a deodorizing effect.

When citronellyl formate and phenylethyl formate are used, the content thereof is preferably 1% by mass or more and 10% by mass or less of the mass of a fragrant agent used per roll in a toilet roll. Within this range, fragrance can be sufficiently felt, and a deodorizing effect can be obtained.

On the other hand, when the volatile deodorizing fragrant agent contains at least one of the above citronellyl formate and phenylethyl formate, it is desirable that the volatile deodorizing fragrant agent does not contain vanillin. Vanillin, which is a kind of fragrant agent, has a sweet vanilla fragrance, has poor affinity with fragrance of citronellyl formate and phenylethyl formate, and makes it difficult to recognize sustainability of an effect of masking an ammonia odor or an effect due to a decrease in fragrance. Therefore, use of vanillin together with citronellyl formate and phenylethyl formate is not desirable. Meanwhile, vanillin has affinity with limonene, menthol, and the like, which have a refreshing fragrance. Use of vanillin together with limonene, menthol, and the like is desirable in terms of recognizing sustainability of a deodorizing effect by fragrance.

On the other hand, in the toilet roll according to the present invention, a volatile deodorizing fragrant agent is applied to an outer surface of a paper tube, and a deodorizing region to which a deodorant that chemically deodorizes a malodorous component is applied for deodorizing a malodorous component by contact with the malodorous component is provided on an inner periphery of the paper tube. It is desirable that this deodorizing region is located on the entire inner periphery of the paper tube. The wider the region is, the higher a chance of contact with a malodorous component is. In the toilet roll according to the present invention, two deodorizing effects brought by a volatile component from the outer periphery of the paper tube and contact on the inner surface of the paper tube are imparted to the paper tube, the two deodorizing effects are imparted to different positions, and a high deodorizing effect and fragrance can be felt. The toilet roll according to the present invention has an excellent immediate effect on a malodorous component such as ammonia diffused in a toilet space, an excellent deodorizing effect on an odor source, and excellent sustainability of the deodorizing effect. Furthermore, the toilet roll according to the present invention makes it easy to recognize exhibition of the deodorizing effect.

Here, the toilet roll according to the present invention has a deodorizing region impregnated with a volatile deodorizing fragrant agent and a deodorant. However, even when the volatile deodorizing fragrant agent and the deodorant are combined, the deodorizing effects thereof are not decreased. Furthermore, in the combination according to the present invention, the fragrant agent also exhibits a deodorizing effect. Therefore, the amount of the fragrant agent or the deodorant used can be reduced, the degree of freedom in design can be increased, and cost can be reduced. Furthermore, the volatile deodorizing fragrant agent deodorizes a space. In a situation of frequently visiting a toilet space or easy volatilization of the volatile deodorizing fragrant agent due to a high temperature in the toilet space, the deodorizing region supplements space deodorization. Therefore, a deodorizing action is efficiently exhibited.

Here, it is desirable that the deodorant contains any one of polyphenol, a polyphenol derivative, and a polyphenol analog (hereinafter, also referred to as a polyphenol or the like). The polyphenol or the like is extracted from plants and processed products of plants, and has a deodorizing function on ammonia, which is one of main malodorous components present at least in a toilet space, due to reactivity of a phenolic hydroxy group. Of course, there is a substance having reactivity with hydrogen sulfide, methyl mercaptan, and trimethylamine known as malodorous components in a toilet space in addition to ammonia and having a deodorizing function thereon. The polyphenol or the like may be such a substance. For example, among polyphenol derivatives, as disclosed in JP 3919729 B2, there is a known substance obtained by artificially adding an appropriate functional group to a polyphenol having a high molecular weight to impart or enhance a deodorizing function on a specific component. The polyphenol or the like according to the present invention may be such a substance.

In the toilet roll according to the present invention, particularly, when the polyphenol or the like is used as the deodorant and the ester-based compound is used as the volatile deodorizing substance, a deodorizing effect can be obtained by different deodorizing actions of a deodorizing action due to reactivity of a phenolic hydroxy group and a deodorizing action due to an exchange reaction of the ester-based compound. Therefore, the toilet roll according to the present invention is highly desirable. Furthermore, the polyphenol or the like does not affect fragrance or a deodorizing effect of the ester-based compound. Particularly, the combination of the polyphenol or the like with citronellyl formate and phenylethyl formate is desirable in terms of fragrance and effect.

Here, it is desirable that a paper tube is impregnated with the polyphenol or the like and holds the polyphenol or the like in a thickness direction from an internal surface side of the paper tube to an outer peripheral surface side thereof.

Contact with a malodorous component floating in a toilet space is sufficiently ensured through the inner surface of the paper tube, and the excellent deodorizing function of the polyphenol or the like can be more effectively exhibited. Note that paper is not easily impregnated with the polyphenol or the like, but can be impregnated with the polyphenol or the like when the polyphenol or the like is applied to the paper together with a lower alcohol such as ethanol, methanol, butanol, or propanol.

More preferable specific examples of the polyphenol or the like include tannin, catechin, rutin, anthocyanin, ellagic acid, coumarin, flavone, and derivatives or precursors thereof. These substances exhibit a particularly high deodorizing effect on a malodorous component of a toilet, and does not affect fragrance of the volatile deodorizing fragrant agent which is the ester-based compound. Note that the paper tube may be appropriately impregnated with a plurality of the substances.

Among the above specific examples, tannin and a derivative thereof are particularly preferable. Tannin and a tannin derivative each have a large molecular weight and a large number of phenolic hydroxy groups, and therefore have an excellent deodorizing function. Note that tannin may be either condensed tannin or hydrolyzed tannin. Among the kinds of tannin, a persimmon tannin derived from a persimmon has a very large molecular weight and has an extremely excellent deodorizing effect. Therefore, at least one of the persimmon tannin and the persimmon tannin derivative is preferably included as the deodorant component according to the present invention. When the persimmon tannin is included, a tea catechin is preferably further included together with the persimmon tannin.

Note that the polyphenol or the like may be derived from a commercially available polyphenol-based deodorant. Examples of the commercially available polyphenol-based deodorant include Pancil COS-15, Pancil COS-17, Pancil CL-10, Pancil AS-10, Pancil AS-20, Pancil BA-210-1, Pancil COS-5, Pancil FG-22, Pancil FG-25, Pancil FG-30, Pancil FG-60, Pancil FG-70, Pancil FG-99, Pancil FX10, Pancil P0-10, and Pancil BA-200E-1, manufactured by Release Kagaku Kogyo Co., Ltd.

On the other hand, the toilet roll according to the present invention may contain an organic acid or an organic acid salt in addition to the volatile deodorizing fragrant agent and the polyphenol or the like as long as the effect of the present invention is not impaired. An organic acid and an organic acid salt also have a deodorizing effect. It is desirable that the organic acid and the organic acid salt have high safety to a human body, and examples thereof include lactic acid, tartaric acid, malic acid, fumaric acid, succinic acid, citric acid, glutaric acid, amino acid, adipic acid, ascorbic acid, inorganic salts thereof, and organic salts thereof. Examples of an inorganic base that forms a salt include a hydroxide, an oxide, a carbonate, and a hydrogen carbonate of an alkali metal or an alkaline earth metal such as sodium, potassium, lithium, calcium, or magnesium. Examples of the organic base include a nitrogen-containing base such as a primary, secondary, or tertiary amine or a compound having an imino group, a guanidino group, an imidazolino group, an imidazolyl group, or a pyridyl group.

On the other hand, if the paper tube is impregnated with the polyphenol or the like together with the volatile deodorizing fragrant agent, it is desirable that the paper tube is obtained by spirally winding one to three paper tube base sheets and has a paper thickness of 100 to 1200 μm and a basis weight of 130 to 618 g/m². By setting the paper thickness and the basis weight in these ranges, the density is appropriate, contact of the polyphenol or the like with a malodorous component floating in a toilet space is ensured, and an excellent deodorizing function of the polyphenol or the like can be effectively exhibited. In addition, a sufficient amount of volatile deodorizing fragrant agent can be included. Particularly, it is desirable that the paper tube is obtained by spirally winding two paper tube base sheets and has a paper thickness of 200 to 800 μm and a basis weight of 130 to 412 g/m². Such a paper tube is easily manufactured, and has excellent contact particularly with the polyphenol or the like. Note that the thickness of the paper tube and the basis weight thereof are measured in a state of the paper tube. Although the paper tube has a cylindrical shape, an error due to its bending can be ignored if the paper tube has an inner diameter within the above range.

Furthermore, in the toilet roll according to the present invention, it is desirable that the paper tube 11 has a Bekk smoothness of 10 to 80 seconds measured by the method described in JIS P 8119 (1998). A paper tube having a Bekk smoothness of 10 to 80 seconds reliably holds a deodorant with which the paper tube is impregnated, and also sufficiently ensures contact of the polyphenol or the like with which the paper tube is impregnated with a malodorous component such as ammonia floating in a toilet space.

It is desirable that the content of the polyphenol or the like according to the present invention is 0.002 to 6.0 g/m² based on the area of the inner peripheral surface of the paper tube. The content of the polyphenol or the like is more preferably 0.2 to 2 g/m². With this content, a deodorizing effect of the polyphenol or the like can be sufficiently exhibited.

On the other hand, it is desirable that the toilet roll according to the present invention is packaged in a packaging bag having a high gas barrier property to be formed into a product since the volatile deodorizing fragrant agent is volatilized into a toilet space.

EXAMPLES

In order to confirm the effect of the present invention, by using Example 1 and Comparative Examples 1 to 4, a deodorizing effect on ammonia, which is one of main malodorous components in a toilet space, was tested and confirmed by the following procedures (1) to (4).

(1) In a 20 L airtight container (Tedlar bag 20 L: manufactured by GL Science Co., Ltd.), 20 μL of 25% ammonia water (manufactured by Wako Pure Chemical Industries, Ltd., first grade) is put, and then air is put therein and the airtight container is sealed. The 20 L airtight container is allowed to stand for 60 minutes to volatilize ammonia therein, thus preparing a 20 L airtight container filled with ammonia gas.

(2) A paper tube (basis weight: 160 g/m², inner diameter: 41 mmcp×114 mm) having an inner surface impregnated with Pansil FG28 and Beamstar OF, which are polyphenol-based deodorants, is prepared.

(3) A sample obtained by applying 120 μL of a fragrant agent (FRUITY 714018227: manufactured by Takasago International Corporation) containing a volatile deodorizing component having a concentration of 1% to an outer surface of the paper tube prepared in (2) (Example 1), a sample obtained by applying 120 μL of a fragrant agent (FRUITY 714018227: manufactured by Takasago International Corporation) containing a volatile deodorizing component having a concentration of 5% to an outer surface of the paper tube prepared in (2) (Example 2), a sample obtained by applying 120 μL of a fragrant agent (FRUITY 714018227: manufactured by Takasago International Corporation) containing a volatile deodorizing component having a concentration of 10% to an outer surface of the paper tube prepared in (2) (Example 3), a blank sample to which neither a polyphenol-based deodorant nor a fragrant agent containing a volatile deodorizing component is applied to an outer surface of the paper tube prepared in (2) (Comparative Example 1), a sample to which 120μ of a conventional fragrant agent that does not chemically react with ammonia (TJP-0-4761: manufactured by Takasago International Corporation) is applied to an outer surface of the paper tube prepared in (2) (Comparative Example 2), and a sample to which 120 μL of a conventional fragrant agent that does not chemically react with ammonia (FIVENEO C-7278: manufactured by Soda Aromatic Co., Ltd.) is applied to an outer surface of the paper tube prepared in (2) (Comparative Example 3) are prepared, and each of the samples is immediately put in a closed container and sealed. Note that the volatile deodorizing fragrant agent used in Examples 1 to 3 does not contain vanillin but contain citronellyl formate.

(4) The ammonia gas prepared in (1) is put in the sealed closed container containing each of the samples such that the concentration is 130 ppm, and the closed container is sealed.

(5) After the closed container is allowed to stand for 15 minutes, which is a short time, and after the closed container is allowed to stand for 60 minutes, the ammonia gas concentration in the airtight container related to the sample in each of examples is measured, and an ammonia decomposing effect is confirmed. Note that the ammonia gas concentration was measured using a gas detector tube (3 L manufactured by Gastec Co., Ltd.). The results are illustrated in Table 1 below.

TABLE 1

| Sample name | 0 min | 15 min | 60 min |
| --- | --- | --- | --- |
| Comparative Example 1 | 130 ppm | 130 ppm | 130 ppm |
| Comparative Example 2 | 130 ppm | 40 ppm | 30 ppm |
| Comparative Example 3 | 130 ppm | 40 ppm | 30 ppm |
| Example 1 | 130 ppm | 30 ppm | 20 ppm |
| Example 2 | 130 ppm | 25 ppm | 15 ppm |
| Example 3 | 130 ppm | 20 ppm | 10 ppm |

With reference to Table 1, in the samples in Examples 1 to 3 according to the present invention, the ammonia concentration was significantly decreased after 15 minutes, which is a short time, as compared with Comparative Examples. In addition, there was a significant difference even after 60 minutes. It has been confirmed that the volatile deodorizing fragrant agent according to the present invention exhibits a deodorizing effect continuously after 15 minutes, which is a short time. From this, it has also been confirmed that the volatile deodorizing fragrant agent is volatilized and the container is filled with the volatile deodorizing fragrant agent. From the results, it can be said that no deodorant is detached from the toilet roll according to the present invention, and the toilet roll according to the present invention has an excellent immediate effect on a malodorous component such as ammonia diffused in a toilet space and an excellent deodorizing effect on an odor source. In addition, it can be said that the toilet roll according to the present invention makes it easy to recognize exhibition of the deodorizing effect by fragrance.

REFERENCE SIGNS LIST

10 Toilet roll
11 Paper tube
11A Inner surface of paper tube
S3 Toilet paper
L1 Width of toilet roll
L2 Diameter of toilet roll

The invention claimed is:

1. A toilet roll comprising:
a paper tube having a Bekk smoothness of 10 to 80 seconds measured by the method described in JIS P 8119 (1998); and
belt shaped toilet paper wound around the paper tube,
wherein a volatile deodorizing fragrant agent that is vaporized to emit fragrance and chemically deodorizes a malodorous component by changing the malodorous component into a substance having no or little malodor through chemical reaction is applied to an outer periphery of the paper tube, and a deodorizing region to which a deodorant that chemically deodorizes a malodorous component is applied for deodorizing a malodorous component by contact with the malodorous component is provided on an inner periphery of the paper tube,
wherein the volatile deodorizing fragrant agent contains one or more kinds of ester-based compounds including an ester-based compound having a vapor pressure in a range of 0.02 mmHg or more and less than 0.1 mmHg at 20° C.,
wherein the deodorant contains any one of a polyphenol, a polyphenol derivative, and a polyphenol analog, the one of the polyphenol, the polyphenol derivative, and the polyphenol analog containing at least persimmon tannin and tea catechin, and
wherein a content of the one of the polyphenol, the polyphenol derivative, and the polyphenol analog is 0.002 to 6.0 g/m$^2$ based on an area of the inner periphery of the paper tube.

2. The toilet roll according to claim 1, wherein the one or more kinds of ester-based compounds is selected from the group consisting of linalyl acetate, eugenyl acetate, geranyl acetate, savinyl acetate, sabinene hydrate, citronellyl acetate, terpinyl acetate, neryl acetate, butyl algerate, vetiberyl acetate, benzyl acetate, benzyl benzoate, bornyl acetate, bornyl isovalerate, methyl anthranilate, methyl salicylate, methyl butyrate, methyl benzoate, menthyl acetate, labansuryl acetate, and formate.

3. The toilet roll according to claim 1, wherein the volatile deodorizing fragrant agent contains at least one of citronellyl formate and phenylethyl formate and does not contain vanillin.

* * * * *